United States Patent
Winkelmann

(10) Patent No.: US 6,932,507 B2
(45) Date of Patent: Aug. 23, 2005

(54) METHOD FOR THE SELECTION OF A NEW DETECTOR MODULE FOR X-RAY COMPUTER TOMOGRAPHY

(75) Inventor: Helmut Winkelmann, Eggolshiem (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/485,952

(22) PCT Filed: Aug. 2, 2002

(86) PCT No.: PCT/DE02/02854
§ 371 (c)(1),
(2), (4) Date: Feb. 6, 2004

(87) PCT Pub. No.: WO03/015632
PCT Pub. Date: Feb. 27, 2003

(65) Prior Publication Data
US 2004/0190683 A1 Sep. 30, 2004

(30) Foreign Application Priority Data
Aug. 8, 2001 (DE) .......................... 101 38 922

(51) Int. Cl.$^7$ .............................................. G01D 18/00
(52) U.S. Cl. .............................. 378/207; 378/19; 378/4
(58) Field of Search ............................ 378/4, 19, 98.8, 378/207; 250/370.08, 307.09

(56) References Cited

U.S. PATENT DOCUMENTS

| | | | |
|---|---|---|---|
| 5,944,770 A | 8/1999 | Enge et al. | 257/679 |
| 6,137,859 A | 10/2000 | Von Der Haar et al. | 378/19 |
| 6,275,559 B1 * | 8/2001 | Ramani et al. | 378/4 |
| 6,325,540 B1 | 12/2001 | Lounsberry et al. | 378/207 |

FOREIGN PATENT DOCUMENTS

| | | |
|---|---|---|
| DE | 3732820 | 4/1989 |
| DE | 19502574 | 8/1996 |
| DE | 10057625 | 5/2001 |
| EP | 0677721 | 10/1995 |
| JP | 10213667 | 8/1997 |

* cited by examiner

*Primary Examiner*—Edward J. Glick
*Assistant Examiner*—Courtney Thomas
(74) *Attorney, Agent, or Firm*—Harness, Dickey & Pierce, P.L.C.

(57) ABSTRACT

A method is for selection of a new detector module as replacement for a detector module built in to a detector of an X-ray computer tomograph. The method includes production of the detector module, using component with an unique electronically-stored code and generation of a data set containing the essential parameters of each detector module with reference to the code of each detector module. The method further includes storage of the data set and the codes in an electronic databank and electronic reading of the code of the detector module for exchange and comparison of the relevant stored data set with the data sets for new detector modules. Finally, the method includes selection of a new detector module according to set selection criteria.

15 Claims, 1 Drawing Sheet

METHOD FOR THE SELECTION OF A NEW DETECTOR MODULE FOR X-RAY COMPUTER TOMOGRAPHY

This application is the national phase under 35 U.S.C. § 371 of PCT International Application No. PCT/DE02/02854 which has an International filing date of Aug. 2, 2002, which designated the United States of America and which claims priority on German Patent Application number DE 101 38 922.1 filed Aug. 8, 2001, the entire contents of which are hereby incorporated herein by reference.

FIELD OF THE INVENTION

The invention generally relates to a method for selecting a new detector module. More preferably, it relates to a method for selecting one as a replacement for a detector module installed in a detector in an X-ray computer tomograph.

BACKGROUND OF THE INVENTION

DE 195 02 574 A1 discloses a detector having a plurality of parallel detector lines which run in the direction of the axis of an object which is to be X-rayed, e.g. a patient. A plurality of detector lines can be in the form of an installation unit or in the form of a detector module. In this case, a printed circuit board holds a sensor array formed from a multiplicity of sensor elements.

The detector modules have different properties, depending on their manufacture. By way of example, the persistence and the drift of the scintillator elements used may vary. In order to provide a detector having the highest possible quality, it is designed using previously selected detector modules having properties which are as similar as possible.

To select the detector modules, they are first labeled manually or are provided with a bar code sticker. In addition, a database is created which stores the fundamental characteristics of the detector module in a data record under the respective identifier attached.

If a detector module in a detector needs to be replaced with a new detector module, it has previously been necessary to open the detector housing and to read off the often poorly accessible identifier attached to the respective detector module. The identifier and the previously created database are then used to select a suitable new detector module, which is substituted at the subsequent time in a second repair step for the detector module which is to be replaced.

The known method is disadvantageous in many respects: when detector modules are labeled manually, they may become damaged. Until the detector modules have been provided with an identifier, there is the risk of their being mixed up. Reading off identifiers on installed detector modules requires the detector housing to be opened. Replacing a detector module necessitates further time-consuming action in the computer tomographs. Finally, the identifier used in line with the prior art can be forged. Detector modules can be duplicated without the manufacturer's authorization.

U.S. Pat. No. 5,994,770 discloses a component for storing data for identifying products. The known component can be read out electronically.

SUMMARY OF THE INVENTION

It is an object of an embodiment of the invention to reduce or even eliminate the drawbacks based on the prior art. In particular, the aim is to specify a method which allows simplified and rapid replacement of detector modules with suitable new detector modules in a detector in an X-ray computer tomograph.

An embodiment of the invention provides a method for selecting a new detector module as a replacement for a detector module installed in a detector in an X-ray computer tomograph, having the following steps:
a) the detector modules are manufactured using a component which contains a unique electronically stored identifier,
b) a data record containing the fundamental characteristics of each of the detector modules is created with reference to the identifier of the respective detector module,
c) the data records and the identifiers are stored in an electronic database,
d) the identifier of the detector module to be replaced is read out electronically and the data record stored therefor is compared with the data records of new detector modules, and
e) a new detector module is selected according to prescribed selection criteria.

By manufacturing the detector modules immediately using a component which contains a unique electronically stored identifier, any damage as a result of subsequent labeling is avoided. Likewise, mix-ups are prevented.

In addition, it is possible immediately after manufacture to start creating a detector-specific data record which contains all the fundamental data relating to manufacture. This makes it possible to find new detector modules which are particularly similar. In this case, the selection is made according to prescribed selection criteria. The selection criteria can be, by way of example, a prescribed similarity pattern for particular parameters, such as the drift or the persistence. Such a selection pattern may be of hierarchic structure. The selection can be made using the prescribed selection criteria automatically using a computer.

In line with one advantageous refinement of the method, the data record is used to store information about all the fundamental processing steps in the detector module. It is thus possible, by way of example, to store information about the batch of scintillator elements used or other characteristics of components used, which characteristics influence the property of the detector module. In addition, the data record can be used to store the fundamental characteristics of the detector array in the detector module. These are, by way of example, temperature-dependent parameters such as drift and persistence.

In accordance with another refinement, the data record is used to store a value which indicates the association with one of a plurality of prescribed quality classes. This simplifies and speeds up the finding of detector modules having comparable properties.

Advantageously, the component generates a time signal, and a signal containing the identifier is generated after a prescribed period of time has elapsed. The signal can indicate, by way of example, the end of a prescribed replacement period. It is also possible to ascertain the working hours of a detector module. It is regarded as particularly advantageous that the signal is transmitted to a central maintenance device by means of remote data transmission and is displayed there. This allows suitable new detector modules to be provided rapidly.

It is also conceivable for the signal to be generated even if, in a routine self-test in the computer tomograph, it is discovered that a detector module no longer satisfies prescribed properties.

BRIEF DESCRIPTION OF THE DRAWINGS

Further advantages, features and details of the invention will become evident from the description of illustrated embodiments given hereinbelow and the accompanying drawing, which is given by way of illustration only and thus is not limitative of the present invention, wherein.

DETAILED DESCRIPTION OF THE PREFERRED EMBODIMENTS

Figure 1:
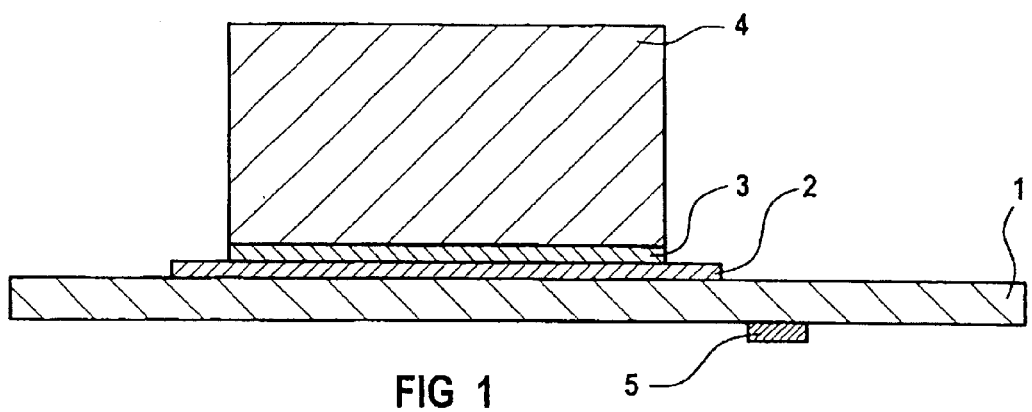
FIG. 1 shows a schematic cross sectional view of a detector module.

FIG. 1 shows a schematic cross section of a detector module. A photodiode array 2 is mounted on a printed circuit board 1. Bonded onto the photodiode array 2 are scintillator elements 3, which are preferably manufactured from a scintillator ceramic. 4 denotes a collimator. A component 5 is mounted on the underside of the printed circuit board 1, the underside being opposite the photodiode array 2. The component 5 stores data, particularly a unique identifier for the detector module. The component 5 can be shielded by a metal plate (not shown in this case) fitted on the reverse of the printed circuit board. This prevents any malfunction of the component 5 as a result of ingressive X-ray radiation.

Figure 2:
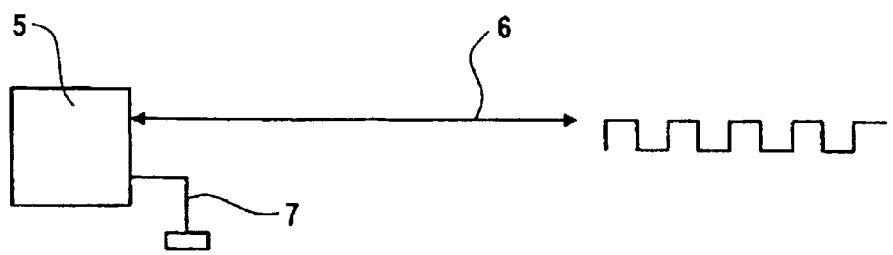
FIG. 2 shows a schematic operational view of a component.

FIG. 2 schematically shows the operation of the component 5. The component is of particularly simple design. The voltage required for operating the component 5 and the data transmission can in this case be provided by way of a single electrical connection 6. The component 5 is connected to ground by means of a further electrical connection 7. A component which is suitable for the purposes of the inventive method is described, by way of example, in U.S. Pat. No. 5,994,770, the entire disclosure content of which is incorporated herein by reference.

What is claimed is:

1. A method for selecting a new detector module as a replacement for a detector module installed in a detector in an X-ray computer tomograph, comprising:
   a) manufacturing the detector modules using a component which contains a unique electronically stored identifier;
   b) creating a data record, containing the fundamental characteristics of each of the detector modules, with reference to the identifier of the respective detector module;
   c) storing the data records and the identifiers in an electronic database;
   d) reading the identifier, of the detector module to be replaced, out electronically and comparing the correspondingly stored data record with the data records of new detector modules; and
   e) selecting a new detector module according to prescribed selection criteria.

2. The method as claimed in claim 1, wherein the data record is used to store information about all the fundamental processing steps in the detector module.

3. The method as claimed in claim 2, wherein the data record is used to store the fundamental characteristics of a detector array in the detector module.

4. The method as claimed in claim 2, wherein the data record is used to store a value which indicates the association with one of a plurality of prescribed quality classes.

5. The method as claimed in claim 2, wherein the component generates a time signal, and a signal containing the identifier is generated after a prescribed period of time has elapsed.

6. The method as claimed in claim 2, wherein the signal is transmitted to a central maintenance device by means of remote data transmission and is displayed there.

7. The method as claimed in claim 1, wherein the data record is used to store the fundamental characteristics of a detector array in the detector module.

8. The method as claimed in claim 7, wherein the data record is used to store a value which indicates the association with one of a plurality of prescribed quality classes.

9. The method as claimed in claim 7, wherein the component generates a time signal, and a signal containing the identifier is generated after a prescribed period of time has elapsed.

10. The method as claimed in claim 7, wherein the signal is transmitted to a central maintenance device by means of remote data transmission and is displayed there.

11. The method as claimed in claim 1, wherein the data record is used to store a value which indicates the association with one of a plurality of prescribed quality classes.

12. The method as claimed in claim 11, wherein the component generates a time signal, and a signal containing the identifier is generated after a prescribed period of time has elapsed.

13. The method as claimed in claim 11, wherein the signal is transmitted to a central maintenance device by means of remote data transmission and is displayed there.

14. The method as claimed in claim 1, wherein the component generates a time signal, and a signal containing the identifier is generated after a prescribed period of time has elapsed.

15. The method as claimed in claim 1, wherein the signal is transmitted to a central maintenance device by means of remote data transmission and is displayed there.

* * * * *